United States Patent
Yanagisawa (10) Patent No.: US 10,012,677 B2
(45) Date of Patent: Jul. 3, 2018

(54) VOLTAGE DETECTING APPARATUS

(71) Applicant: HIOKI DENKI KABUSHIKI KAISHA, Nagano (JP)

(72) Inventor: Koichi Yanagisawa, Nagano (JP)

(73) Assignee: HIOKI DENKI KABUSHIKI KAISHA, Nagano (JP)

(*) Notice: Subject to any disclaimer, the term of this patent is extended or adjusted under 35 U.S.C. 154(b) by 319 days.

(21) Appl. No.: 14/870,603

(22) Filed: Sep. 30, 2015

(65) Prior Publication Data
US 2016/0109486 A1 Apr. 21, 2016

(30) Foreign Application Priority Data

Oct. 17, 2014 (JP) .................. 2014-212900
Dec. 2, 2014 (JP) .................. 2014-243762

(51) Int. Cl.
*G01R 19/18* (2006.01)
*G01R 15/16* (2006.01)
*G01R 1/07* (2006.01)
*G01N 27/90* (2006.01)

(52) U.S. Cl.
CPC .............. *G01R 15/16* (2013.01); *G01R 1/07* (2013.01); *G01N 27/90* (2013.01)

(58) Field of Classification Search
None
See application file for complete search history.

(56) References Cited

U.S. PATENT DOCUMENTS

| 4,878,017 A | 10/1989 | Williams | |
|---|---|---|---|
| 5,151,659 A * | 9/1992 | Tanaka | G01N 27/002 324/457 |
| 6,009,756 A * | 1/2000 | Willems | G01N 27/902 73/592 |
| 6,517,669 B2 * | 2/2003 | Chapman | H01J 37/32935 156/345.25 |
| 2007/0108992 A1 * | 5/2007 | Yanagisawa | G01R 19/20 324/658 |
| 2009/0319210 A1 * | 12/2009 | Yanagisawa | G01R 15/16 324/123 R |

FOREIGN PATENT DOCUMENTS

JP 7-092487 B2 10/1995

* cited by examiner

*Primary Examiner* — Tung X Nguyen
(74) *Attorney, Agent, or Firm* — Greenblum & Bernstein, P.L.C.

(57) ABSTRACT

A voltage detecting apparatus detects a detection voltage generated in a detected object which is covered by an insulator. The voltage detecting apparatus includes: a detection electrode that is disposed so as to contact the insulator directly, or indirectly via another insulator; a vibrator that causes the insulator to vibrate; a current-to-voltage converter circuit that converts a detection current to a detection voltage signal, the detection current flowing from the detected object via the detection electrode to a reference voltage in a state where the insulator is being caused to vibrate, having an amplitude that is modulated in accordance with a potential difference between the detection voltage and the reference voltage, and being synchronized with vibration of the vibrator; and a detector circuit that detects a detection output indicating the potential difference from the detection voltage signal.

16 Claims, 5 Drawing Sheets

VOLTAGE DETECTING APPARATUS

1. FIELD OF THE INVENTION

The present invention relates to a contactless voltage detecting apparatus that detects the voltage of a detected object that is covered with an insulating material via the insulating material.

2. DESCRIPTION OF THE RELATED ART

As a contactless voltage detecting apparatus, the voltage detecting apparatus (contactless capacitance follower) disclosed in Japanese Examined Patent Application Publication No. H07-92487 is known. This voltage detecting apparatus is equipped with a probe for detecting voltage. The probe includes a detection electrode disposed so as to face a measurement surface (i.e., the surface of the detected object) having a capacitance to be measured, a modulator/driving means that operates in conjunction with the detection electrode to modulate the capacitive coupling between the detection electrode and the measurement surface, and means for defining a path of radiation toward the measurement surface in order to radiate a section of the measurement surface that matches the detection electrode.

The detection electrode is housed inside a housing. The housing is also provided with a first aperture/window so that the detection electrode is exposed to the measurement surface via the first aperture/window. The detection electrode is connected by a wire to a + input terminal (inverting input terminal) of an amplifier (an operational amplifier for converting current to voltage) housed inside the housing, and an non-inverting input terminal of the amplifier is connected by a wire to the housing which is used as the reference potential. As one example, it is possible to use a piezoelectric transducer as the modulator/driving means, and by mechanically driving (vibrating) the detection electrode that operates in conjunction with the modulator/driving means, the capacitance (coupling capacitance) formed between the measurement surface and the detection electrode is modulated.

When such capacitance is being modulated, this voltage detecting apparatus equipped with a probe is capable of contactlessly detecting the voltage of the measurement surface based on the capacitance and the current flowing via a resistor which is connected as a current-to-voltage convertor between the + input terminal (inverting input terminal) of the amplifier and the output terminal.

SUMMARY OF THE INVENTION

However, by investigating the voltage detecting apparatus described above, the present inventor discovered the following problem to be solved with the voltage detecting apparatus. With such voltage detecting apparatus, it is necessary to dispose the probe on the measurement surface so that the detection electrode is exposed to the measurement surface through the first aperture (or window) provided in the housing. If the first aperture were covered with an insulator, charge would also theoretically appear on the surface of such insulator due to the influence of the voltage of the measurement surface, but such charge appearing on the surface of the insulator would quickly escape and be lost. Accordingly, there is the problem with the above voltage detecting apparatus that it is not possible to detect the voltage of the measurement surface when an insulator is present between the measurement surface and the detection electrode.

The present invention was conceived to solve the problem described above and it is a primary object of the present invention to provide a voltage detecting apparatus capable of contactlessly detecting the voltage of a detected object even when an insulator is present between the detected object and the detection electrode.

To achieve the stated object, a voltage detecting apparatus according to the present invention that detects a detection voltage generated in a detected object which is covered by an insulator, the voltage detecting apparatus comprises: a detection electrode that is disposed so as to contact the insulator directly, or indirectly via another insulator; a vibrator that causes the insulator to vibrate; a current-to-voltage converter circuit that converts a detection current to a detection voltage signal, the detection current flowing from the detected object via the detection electrode to a reference voltage in a state where the insulator is being caused to vibrate, having an amplitude that is modulated in accordance with a potential difference between the detection voltage and the reference voltage, and being synchronized with vibration of the vibrator; and a detector circuit that detects a detection output indicating the potential difference from the detection voltage signal.

According to the voltage detecting apparatus according to the present invention, by generating the detection current between the detected object and the detection electrode by vibrating the insulator with the vibrator in a state where the detection electrode is directly or indirectly in contact and detecting the voltage to be detected of the detected object based on the detection current, it is possible to detect the voltage to be detected contactlessly (i.e., without the detection electrode directly contacting the detected object), even when an insulator is present between the detected object and the detection electrode.

Also, the voltage detecting apparatus according to the present invention, the detector circuit detects the detection output by detecting the detection voltage signal in synchronization with a synchronization signal that is synchronized with the detection voltage signal. By using such configuration, it is possible to detect and output the detection output in a state where external disturbances have little influence.

Also, the voltage detecting apparatus according to the present invention, the current-to-voltage converter circuit includes an operational amplifier whose first input terminal is set at the reference voltage, whose second input terminal is connected to the detection electrode, which has a feedback circuit connected between the second input terminal and an output terminal, and which converts the detection current flowing in the feedback circuit to the detection voltage signal. By using such configuration, it is possible to sensitively detect the detection current and convert the detection current to the detection voltage signal.

Also, the voltage detecting apparatus according to the present invention comprises a case which is formed of an insulating material and inside which the detection electrode, the vibrator, the current-to-voltage converter circuit, and the detector circuit are disposed, wherein the detection electrode is disposed on an inner surface of a wall portion, out of a plurality of wall portions that construct the case, whose outer surface is placed in contact with the insulator with the wall portion as the other insulator, and the vibrator is fixed to an inner surface of one wall portion out of the plurality of wall portions and causes the case to vibrate. By using such configuration, it is possible to eradicate the burden of separately placing the detection electrode and the vibrator in contact with the insulator, which makes it possible to perform detection operations of the voltage to be detected more efficiently.

Also, the voltage detecting apparatus according to the present invention comprises a shield member that covers the detection electrode, the vibrator, the current-to-voltage converter circuit, and the detector circuit. By using such configuration, it is possible to reduce the influence of external disturbances (such as external magnetic fields and external electric fields) on the circuits that construct the voltage detection apparatus, it is possible to detect and output the detection output in a state where external disturbances have much less influence.

Also, the voltage detecting apparatus according to the present invention that detects a detection voltage generated in a detected object which is covered by an insulator, the voltage detecting apparatus comprises: a detection electrode that is disposed so as to contact the insulator directly, or indirectly via another insulator; an ultrasonic excitation unit that applies a static magnetic field to the detected object and generates an eddy current at an application position of the static magnetic field on the detection object to induce ultrasound in the detected object in a direction that intersects a surface of the application position; a current-to-voltage converter circuit that converts a detection current to a detection voltage signal, the detection current flowing from the detected object via the detection electrode to a reference voltage in a state where the ultrasound is being induced in the detected object, having an amplitude that is modulated in accordance with a potential difference between the detection voltage and the reference voltage, and being synchronized with the ultrasound; and a detector circuit that detects a detection output indicating the potential difference from the detection voltage signal. By using such configuration, it is possible to detect the voltage to be detected contactlessly (i.e., without the detection electrode directly contacting the detected object), even when an insulator is present between the detected object and the detection electrode.

Also, the voltage detecting apparatus according to the present invention, the ultrasonic excitation unit includes a magnet which generates the static magnetic field and applies the static magnetic field to the detected object to generate a static magnetic field along the surface on an inside of the detected object at the application position, and a coil that generates the eddy current in the detected object based on a supplied alternating current, and induces the ultrasonic that vibrates in a direction perpendicular to the surface of the application position. By using such configuration, since it is possible to generate vibration, which is capable of causing variation in the value of the capacitance of the insulator with the highest efficiency, in the detected object and the insulator, it is possible to increase the level of the detection current flowing from the detected object via the detection electrode to the reference potential. As a result, it is possible to sufficiently increase the detection sensitivity for the voltage of the detected object.

Also, the voltage detecting apparatus according to the present invention, the magnet includes: a first magnet that has the coil disposed in a vicinity of a magnetic pole on an application position side; and a second magnet and a third magnet that are disposed so as to sandwich the first magnet and have magnetic poles on an application position side polarized to a different polarity to the magnetic pole of the first magnet. By using such configuration, since it is possible to generate static magnetic fields along the surface of the detected object inside the detected object on both sides of an opposing position that opposes the first end portion of the central magnet at the application position of the static magnetic fields, it is possible to cause the static magnetic fields to have a greater effect relative to the eddy current generated in the periphery of such opposing position. As a result, it is possible to generate stronger ultrasound and in turn to generate stronger vibration inside the detected object. By doing so, according to the voltage detection apparatus it is possible to significantly raise the level of the detection current that flows from the detected object via the detection electrode to the reference potential. As a result, it is possible to significantly raise the detection sensitivity for the voltage of the detected object.

Also, the voltage detecting apparatus according to the present invention, the detector circuit detects the detection output by detecting the detection voltage signal in synchronization with a synchronization signal that is synchronized with the detection voltage signal. By using such configuration, it is possible to detect and output the detection output in a state where external disturbances have little influence.

Also, the voltage detecting apparatus according to the present invention, the current-to-voltage converter circuit includes an operational amplifier whose first input terminal is set at the reference voltage, whose second input terminal is connected to the detection electrode, which has a feedback circuit connected between the second input terminal and an output terminal, and which converts the detection current flowing in the feedback circuit to the detection voltage signal. By using such configuration, it is possible to sensitively detect the detection current and convert the detection current to the detection voltage signal.

It should be noted that the disclosure of the present invention relates to the contents of Japanese Patent Application 2014-212900 that was filed on Oct. 17, 2014 and Japanese Patent Application 2014-243762 that was filed on Dec. 2, 2014, the entire contents of which are herein incorporated by reference.

BRIEF DESCRIPTION OF THE DRAWINGS

These and other objects and features of the present invention will be explained in more detail below with reference to the attached drawings, wherein.

DESCRIPTION OF THE PREFERRED EMBODIMENTS

Preferred embodiments of a voltage detecting apparatus will now be described with reference to the attached drawings.

First, the configuration of the voltage detecting apparatus will be described with reference to the drawings.

Figure 1:
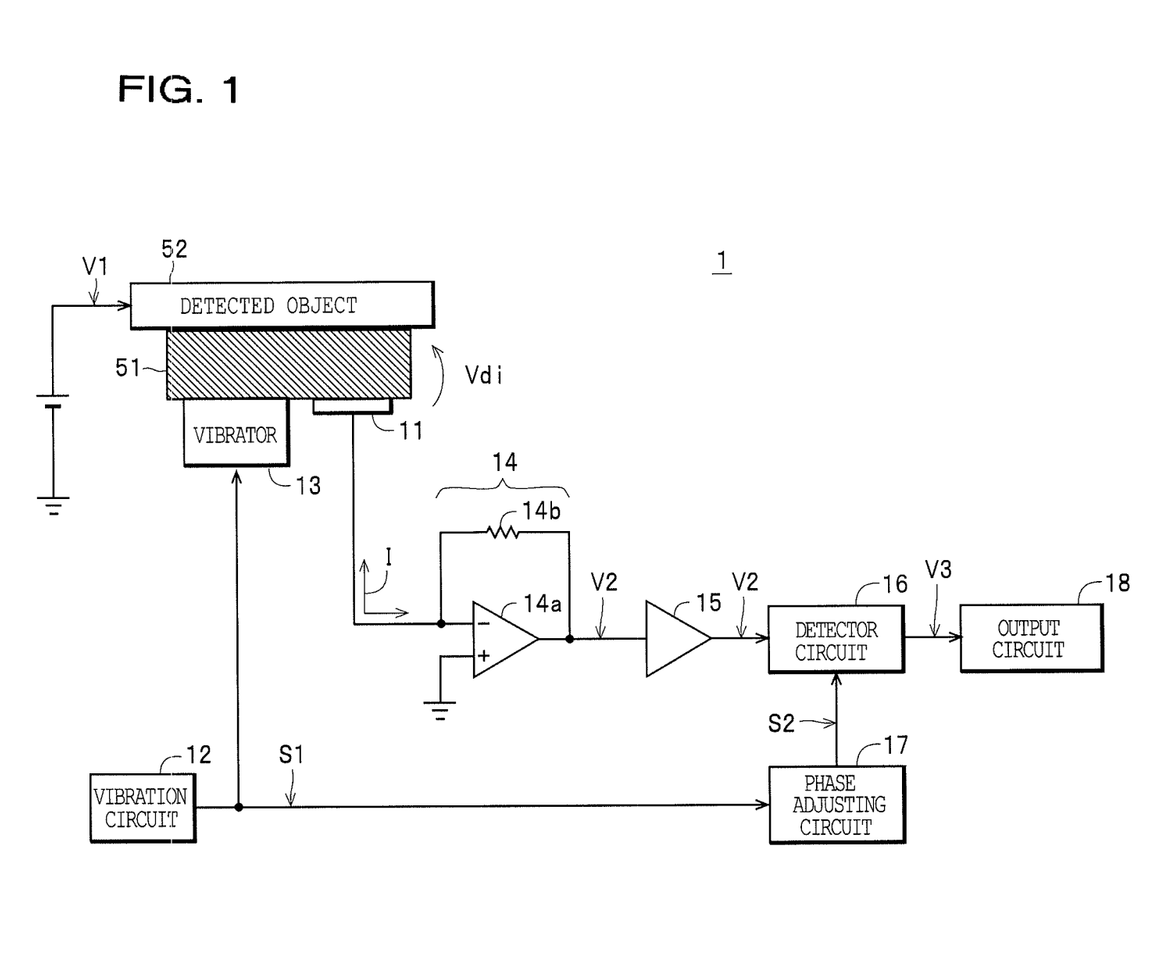
FIG. 1 is a block diagram of a voltage detection apparatus.

The voltage detecting apparatus 1 as the voltage detecting apparatus depicted in FIG. 1 is a contactless voltage detecting apparatus and as one example includes a detection electrode 11, a vibration circuit 12, a vibrator 13, a current-to-voltage converter circuit 14, a buffer amplifier 15, a detector circuit 16, a phase adjusting circuit 17, and an output circuit 18, and is configured so as to be capable of contactlessly detecting a voltage (detected voltage) V1 generated in a detected object 52 covered with an insulator 51.

Figure 2:
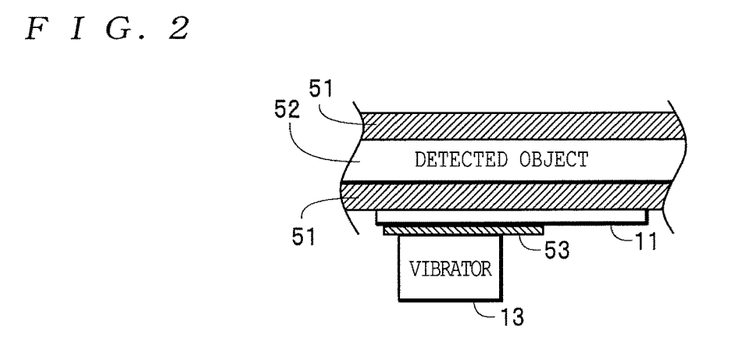
FIG. 2 is a diagram useful in explaining another arrangement of a detection electrode and a vibrator.
Figure 3:
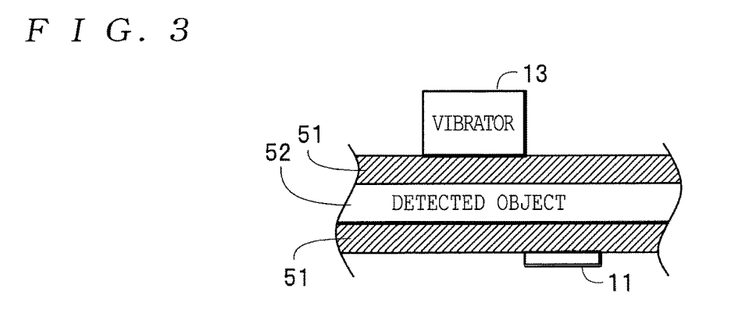
FIG. 3 is a diagram useful in explaining yet another arrangement of a detection electrode and a vibrator.
Figure 4:
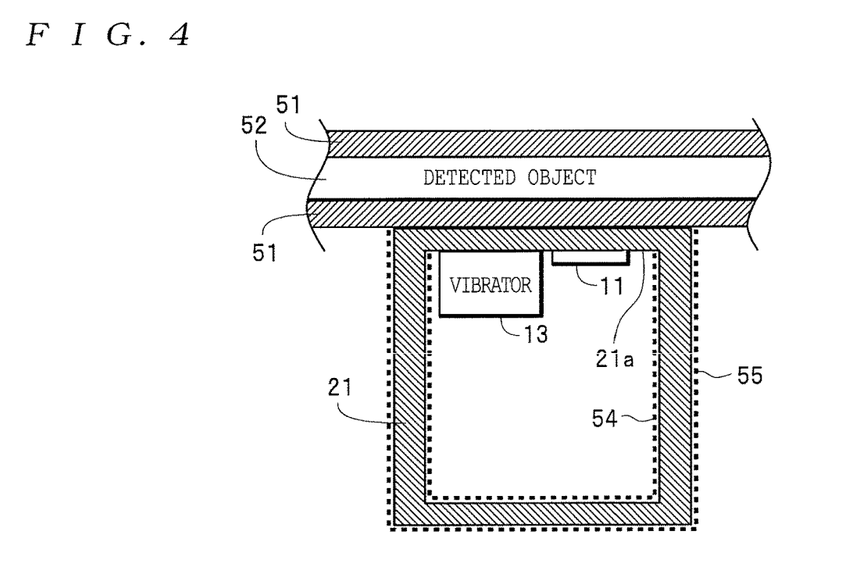
FIG. 4 is a diagram useful in explaining the configuration of a voltage detection apparatus equipped with a case.

Here, as depicted in FIG. 1, a position that forms one part of the surface of the detected object 52 may be covered with the insulator 51 or, as depicted in FIGS. 2, 3, and 4, the entire surface may be covered with the insulator 51 (as one example, the detected object 52 may be the core of a covered electrical cable whose entire outer circumferential surface is covered with an insulating covering). The insulator 51 may have a single-layer construction composed of one type of insulating material, or may have a multi-layer construction where a plurality of layers composed of insulating materials of respectively different types are laminated.

The detection electrode 11 is constructed in a shape that is capable of contacting the surface of the insulator 51 that covers the detected object 52 either directly or indirectly via another insulator (an insulator aside from a gas such as air) disposed in contact (tight contact) with the surface of the insulator 51. Here, it is preferable for the detection electrode 11 to be placed in a state that is as close as possible to tight contact with the surface of the insulator 51. To do so, as examples when the surface of the insulator 51 is flat, corresponding to this the detection electrode 11 is constructed in a shape where a contact surface that contacts the surface of the insulator 51 is also formed flat, while when the surface of the insulator 51 is cylindrical, corresponding to this the detection electrode 11 is constructed so that the contact surface that contacts the surface of the insulator 51 is formed so as to be concave.

As one example, the vibration circuit 12 generates and outputs a driving signal S1 of a certain frequency (predetermined frequency) in a range of around 10 kHz to several MHz. To do so, the vibration circuit 12 is capable of using a configuration that continuously outputs the driving signal S1 during operation, of using a configuration that intermittently and outputs cyclically for a certain period at a time, and of using a configuration that outputs in bursts of a certain length only during measurement. As examples, the vibration circuit 12 outputs a signal that is any of a square wave signal, a triangular wave signal, and a sine wave signal as the driving signal S1. Note that in place of a configuration that generates and outputs the driving signal S1 of a certain frequency as described above, as examples the vibration circuit 12 may use a configuration that generates and outputs a sweep signal whose frequency changes with time in a range between a lower limit frequency and an upper limit frequency that are set in advance as the driving signal S1 or a configuration that generates and outputs a random signal (noise signal) whose frequency changes randomly with time as the driving signal S1.

The vibrator 13 is driven by the driving signal S1 from the vibration circuit 12 and as one example vibrates with the same vibration frequency (in this example, a predetermined frequency) as the frequency of the driving signal S1 and transmits mechanical vibration to a member (in the present embodiment, the insulator) contacted by the vibrator 13. As examples, the vibrator 13 is constructed of an ultrasonic vibrator, a piezoelectric vibrator, a ceramic vibrator, an electromagnetic induction vibrator, a magnetostrictive vibrator, or a vibrator that uses a rotor.

As one example, the current-to-voltage converter circuit 14 includes an operational amplifier 14a and a feedback resistor 14b as a feedback circuit. The non-inverting input terminal (first input terminal) of the operational amplifier 14a is connected to a reference potential (ground) so as to be set at a reference voltage (zero volts), the inverting input terminal (second input terminal) is connected to the detection electrode 11, and the feedback resistor 14b is connected between the inverting input terminal and the output terminal. Note that although a feedback circuit is constructed by a single feedback resistor 14b as one example in the present embodiment, it is also possible to construct a feedback circuit using a series or parallel circuit with a plurality of resistors or a series-parallel circuit that is a combination of a series circuit and a parallel circuit.

As described later, the current-to-voltage converter circuit 14 converts a detection current I to a detection voltage signal V2 and outputs the detection voltage signal V2. The detection current I flows from the detected object 52 via the detection electrode 11 to the reference potential due to a potential difference Vdi (since the reference voltage in the present embodiment is zero volts, the voltage V1) between the voltage V1 of the detected object 52 and the voltage of the detection electrode 11 (since the input terminals of the operational amplifier 14a are virtually shorted, the reference voltage) when the value of the capacitance of the insulator 51 positioned between the detected object 52 and the detection electrode 11 varies due to the vibration from the vibrator 13. The detection current I has a current value in keeping with the magnitude of the potential difference Vdi. That is, the current-to-voltage converter circuit 14 converts the detection current I, which is synchronized with the vibration of the vibrator 13 and whose amplitude is modulated in accordance with the potential difference between the voltage V1 of the detected object 52 and the voltage (reference voltage) of the detection electrode 11, to the detection voltage signal V2.

Here, since the detection current I is generated due to the value of the capacitance of the insulator 51 changing at the vibration frequency of the vibrator 13, the detection current I is an AC signal with the same frequency as the vibration frequency and is generated as an AC signal whose amplitude is modulated to a level in accordance with the potential difference Vdi (in the present embodiment, the voltage V1) described above. This means that the detection voltage signal V2 is outputted from the current-to-voltage converter circuit 14 as an AC signal with the same frequency as the vibration frequency and an amplitude that is modulated to a level in accordance with the potential difference Vdi (in the present embodiment, the voltage V1).

Note that although the current-to-voltage converter circuit 14 that is constructed of the operational amplifier 14a and the feedback resistor 14b and is capable of detecting the detection current I, which typically has an extremely small (minute) amplitude, and converting the detection current I to the detection voltage signal V2 has been described above as an example, the present invention is not limited to such. As one example, when it is desirable to realize the current-to-voltage converter circuit 14 using a simpler configuration, in place of the configuration described above, although not illustrated it is also possible to use a configuration with a resistor with one end connected to the detection electrode 11 and the other end connected to the reference potential (ground). With a current-to-voltage converter circuit 14 of this configuration, the resistor converts the detection current I, which flows from the detected object 52 via the detection electrode 11 to the reference potential (reference voltage), to the detection voltage signal V2. At one end of the resistor, the converted detection voltage signal V2 is outputted to the buffer amplifier 15, described later.

The buffer amplifier 15 is constructed of an amplifier with a high input impedance and a low output impedance, and inputs the detection voltage signal V2 outputted from the current-to-voltage converter circuit 14 with a low impedance. The detector circuit 16 is constructed of a synchronized detection circuit, for example, and by detecting the detection voltage signal V2 inputted from the buffer amplifier 15 in synchronization with a synchronization signal S2 inputted from the phase adjusting circuit 17, detects (extracts) an amplitude component (DC component) of the detection voltage signal V2 and outputs as a detection output (voltage signal) V3. This detector circuit 16 is constructed of any of a multiplier, a selector switch (multiplexer) constructed of an analog switch, and a correlator. Note that it is also possible for the detector circuit 16 to be constructed of an envelope detection circuit, and since the synchronization signal S2 is not necessary when such configuration is used, it is possible to omit the phase adjusting circuit 17.

The phase adjusting circuit 17 inputs and delays the driving signal S1 from the vibration circuit 12 and outputs the driving signal S1 as the synchronization signal S2. The phase adjusting circuit 17 is configured so as to be capable of adjusting the delay between the synchronization signal S2 and the driving signal S1. The delay is adjusted in advance so that the phase of the detection voltage signal V2 as an AC signal inputted into the detector circuit 16 and the phase of the synchronization signal S2 match.

As examples, the output circuit 18 is constructed of a voltmeter that detects and displays the voltage value of the detection output V3, a buffer circuit that inputs the detection output V3 and outputs with a low impedance, or an A/D converter that carries out A/D conversion of the detection output V3 and outputs voltage data that indicates the voltage value of the detection output V3.

Next, a detection operation for the voltage V1 of the detected object 52 carried out by the voltage detection apparatus 1 will now be described. Note that the voltage V1 may be a DC voltage or may be an AC voltage. As one example, it is assumed in the present embodiment that the voltage V1 is a DC voltage.

First, as depicted in FIG. 1, the detection electrode 11 and the vibrator 13 are placed in contact (tight contact) with the surface of the insulator 51 that covers the detected object 52. At this time, as depicted in FIG. 1, both the detection electrode 11 and the vibrator 13 may be moved apart and then placed in contact with the surface on the rear of the insulator 51 relative to the surface that contacts the detected object 52, or as depicted in FIG. 2, the vibrator 13 may be placed in contact (tight contact) with the detection electrode 11 that has been placed in contact with the surface of the insulator 51. Note that as depicted in FIG. 2, when a configuration where the vibrator 13 is placed in contact with the detection electrode 11 is used, to reduce the influence on the detection electrode 11 of an electrical signal generated by the vibrator 13, as depicted in FIG. 2 it is preferable to use a configuration where a shield sheet (for example, a shield that shields against electrical fields and magnetic fields) 53 is interposed between the detection electrode 11 and the vibrator 13. To improve the contact between such members (between the insulator 51 and the detection electrode 11, between the insulator 51 and the vibrator 13, and between the detection electrode 11 (or the shield sheet 53) and the vibrator 13), other insulators (for example, an insulating sheet or gel-type insulator) may be interposed between the members.

Also, as depicted in FIG. 3, with a configuration where the entire outer circumference of the detected object 52 is covered with the insulator 51, it is also possible to place the vibrator 13 in contact with the surface on the rear of the insulator 51 relative to the surface contacted by the detection electrode 11.

In this state, when the driving signal S1 is outputted from the vibration circuit 12, the vibrator 13 is driven by the driving signal S1 and vibrates. By inputting and delaying the driving signal S1, the phase adjusting circuit 17 outputs the synchronization signal S2.

Since the vibration (mechanical vibration) of the vibrator 13 is transmitted to the insulator 51 that is in contact with the vibrator 13, the insulator 51 also vibrates with the same frequency as the vibration frequency of the vibrator 13. In this case, since the distance or the density (i.e., the density of the insulator 51) between the detected object 52 and the detection electrode 11 will vary with the same frequency as the vibration frequency of the vibrator 13, the value of the capacitance of the insulator 51 positioned between the detected object 52 and the detection electrode 11 will vary with the same frequency as the vibration frequency. Due to the variation in the value of the capacitance, the detection current I, which is an AC signal whose amplitude is modulated to a level in keeping with the potential difference Vdi (the voltage V1) and has the same frequency as the vibration frequency, flows on a path including the detected object 52, the detection electrode 11, and the feedback resistor 14*b* of the current-to-voltage converter circuit 14.

The current-to-voltage converter circuit 14 converts the detection current I to the detection voltage signal V2 and outputs the detection voltage signal V2. The buffer amplifier 15 inputs the detection voltage signal V2 outputted from the current-to-voltage converter circuit 14 and outputs with a low impedance. By detecting the detection voltage signal V2 outputted from the buffer amplifier 15 in synchronization with the synchronization signal S2 outputted from the phase adjusting circuit 17, the detector circuit 16 detects the amplitude component (DC component) of the detection voltage signal V2 in a state where external disturbances have little influence and outputs to the output circuit 18 as the detection output (voltage signal) V3. Here, the amplitude component (DC component) of the detection voltage signal V2 detected as the detection output V3 changes in accordance with the potential difference Vdi (in the present embodiment, the voltage V1) described above.

When constructed of an analogue voltmeter, for example, the output circuit 18 inputs the detection output (voltage signal) V3 and, based on the voltage value of the detection output V3 (a voltage value that is proportional to the potential difference Vdi (the voltage V1)), moves a pointer to a value indicating the voltage value of the potential difference Vdi (the voltage V1), thereby outputting in a state where the voltage value of the potential difference Vdi (the voltage V1) can be visually confirmed. When constructed of a buffer circuit, for example, the output circuit 18 inputs the detection output V3 and outputs to the periphery with a low impedance (i.e., outputs to an external measuring instrument or the like so that the voltage value of the potential difference Vdi (the voltage V1) can be detected based on the detection output V3). Also, when constructed of an A/D converter, for example, the output circuit 18 inputs the detection output V3 and outputs voltage data indicating the voltage value of the detection output V3 (which is also voltage data indicating the voltage value of the potential difference Vdi (the voltage V1)) to an internally-provided processing unit (not illustrated) or an external processing apparatus.

In this way, with the voltage detection apparatus 1, by using the vibrator 13 to vibrate the insulator 51 that is in contact with the detection electrode 11, the detection current I is generated and based on the detection current I, the voltage V1 of the detected object 52 is detected. In this way, according to the voltage detection apparatus 1, even when the insulator 51 is present between the detected object 52 and the detection electrode 11, it is possible to detect the voltage V1 of the detected object 52 contactlessly (i.e., without the detection electrode 11 directly contacting the detected object 52).

According to the voltage detection apparatus 1, by outputting the detection output V3 by having the detector circuit 16 detect the detection voltage signal V2 in synchronization with the synchronization signal S2, it is possible to detect and output the detection output V3 in a state where external disturbances have little influence.

Also according to the voltage detection apparatus 1, by constructing the current-to-voltage converter circuit 14 so as to include the operational amplifier 14a and the feedback resistor 14b, it is possible to sensitively detect the detection current I and convert the detection current I to the detection voltage signal V2.

Note that although in the example described above, a configuration where the detection electrode 11 is placed in direct contact with the insulator 51 that covers the detected object 52 is used, since, it is possible for the insulator 51 to have a multilayer structure as described above, as depicted in FIG. 4, it is also possible to use a configuration where the voltage detection apparatus 1 is housed (disposed) inside a case 21 formed of an insulating material so that the detection electrode 11 and the vibrator 13 are not exposed. With this configuration, as depicted in FIG. 4, the detection electrode 11 is disposed on an inner surface of a wall portion 21a, out of the plurality of wall portions that construct the case 21, as another insulator whose outer surface is placed in contact with the insulator 51. Note that although the vibrator 13 may be disposed on any wall portion that constructs the case 21 so long as it is possible for the vibration of the vibrator 13 to be transmitted via the case 21 to the insulator 51, by disposing the vibrator 13 on the same wall portion 21a as the detection electrode 11, it is possible to transmit such vibration to the insulator 51 with the highest efficiency. Note also that component elements aside from the detection electrode 11 and the vibrator 13 have been omitted from FIG. 4.

In this way, by using a configuration where the voltage detection apparatus 1 is housed (disposed) inside the case 21 formed of an insulating material and the detection electrode 11 and the vibrator 13 are not exposed, it is possible to eradicate the burden of separately placing the detection electrode 11 and the vibrator 13 in contact with the insulator 51, which makes it possible to perform detection operations of the voltage V1 more efficiently.

Also, as described above, when a configuration where the voltage detection apparatus 1 is housed inside the case 21 formed of an insulating material is used, as depicted in FIG. 4, it is possible to use a configuration where shield members are disposed on the case 21 (as examples, the shield member 54 on inner surfaces of the case 21 and the shield member 55 on outer surfaces of the case 21). In this case, the shield members are not interposed between the detection electrode 11 and the detected object 52. Also, in FIG. 4, it is possible to use a configuration where only the wall portions of the case 21 where the detection electrode 11 and the vibrator 13 are disposed (i.e., the top wall placed in contact with the insulator 51) is made of an insulating material and the wall portions on which the shield member 54 and the shield member 54 are disposed (i.e., the side walls and bottom wall) are constructed of a shielding material, with such wall portions themselves being used as a shield member. Such shield member is electrically connected to the reference potential (the reference potential to which the non-inverting input terminal of the operational amplifier 14a depicted in FIG. 1 is connected) of the various circuits described above that construct the voltage detection apparatus 1 (i.e., the detection electrode 11, the vibration circuit 12, the vibrator 13, the current-to-voltage converter circuit 14, the buffer amplifier 15, the detector circuit 16, the phase adjusting circuit 17, and the output circuit 18).

According to this configuration, since the voltage detection apparatus 1 is covered by the shield member, it is possible to reduce the influence of external disturbances (such as external magnetic fields and external electric fields) on the various circuits described above that construct the voltage detection apparatus 1 (i.e., the detection electrode 11, the vibration circuit 12, the vibrator 13, the current-to-voltage converter circuit 14, the buffer amplifier 15, the detector circuit 16, the phase adjusting circuit 17, and the output circuit 18), it is possible to detect and output the detection output V3 in a state where external disturbances have much less influence.

Next, another embodiment of a voltage detection apparatus will be described with reference to the attached drawings. Note that elements that are the same as in the embodiment described above have been assigned the same reference numerals.

First, the configuration of the voltage detecting apparatus will be described with reference to the drawings.

Figure 5:
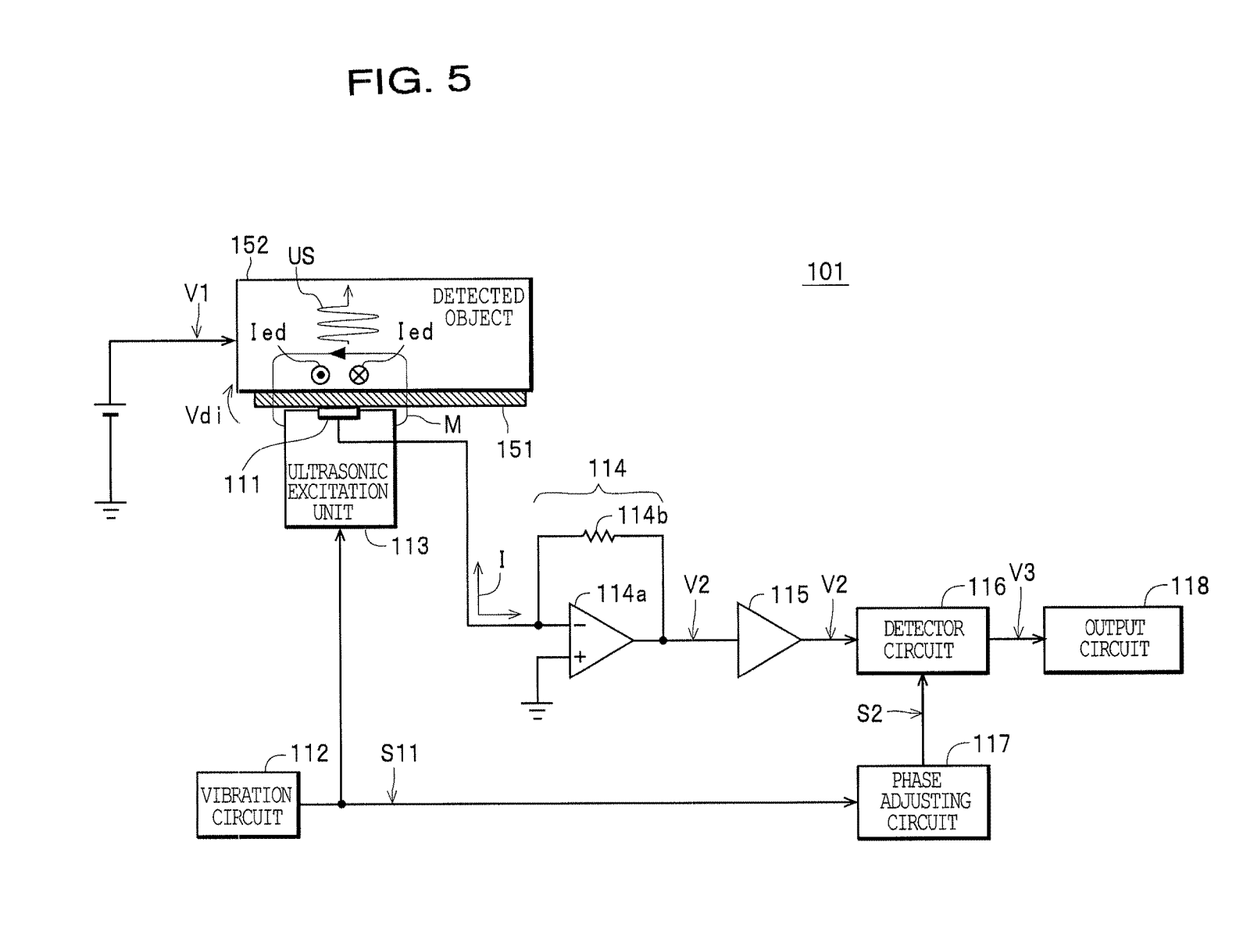
FIG. 5 is a block diagram of another voltage detection apparatus.

The voltage detecting apparatus 101 as the voltage detecting apparatus depicted in FIG. 5 is a contactless voltage detecting apparatus and as one example includes a detection electrode 111, a vibration circuit 112, an ultrasonic excitation unit 113, a current-to-voltage converter circuit 114, a buffer amplifier 115, a detector circuit 116, a phase adjusting circuit 117, and an output circuit 118, and is configured so as to be capable of contactlessly detecting a voltage (detected voltage) V1 generated in a detected object 152 covered with an insulator 151.

Figure 7:
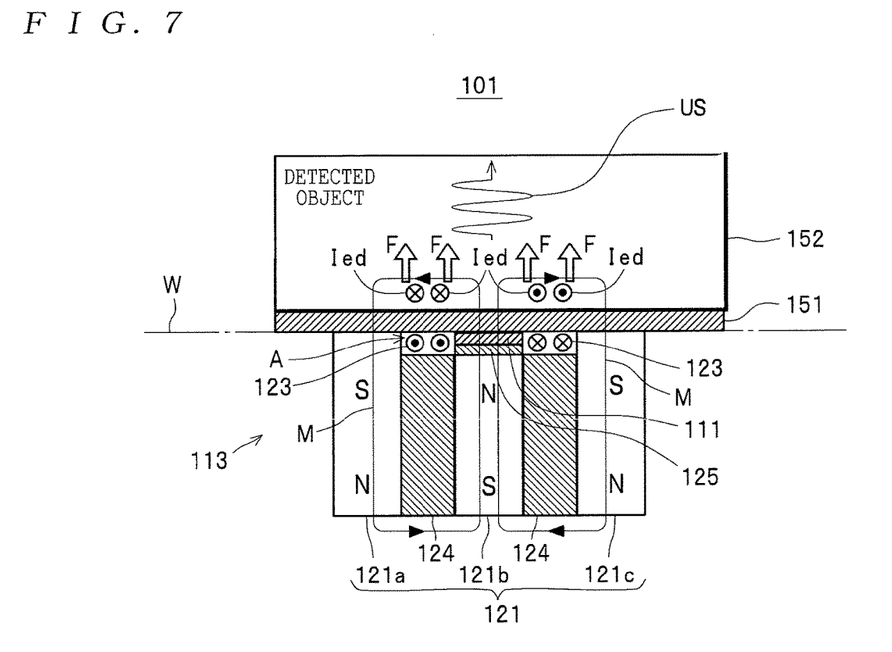
FIG. 7 is a diagram useful in explaining an operation of the voltage detection apparatus.
Figure 8:
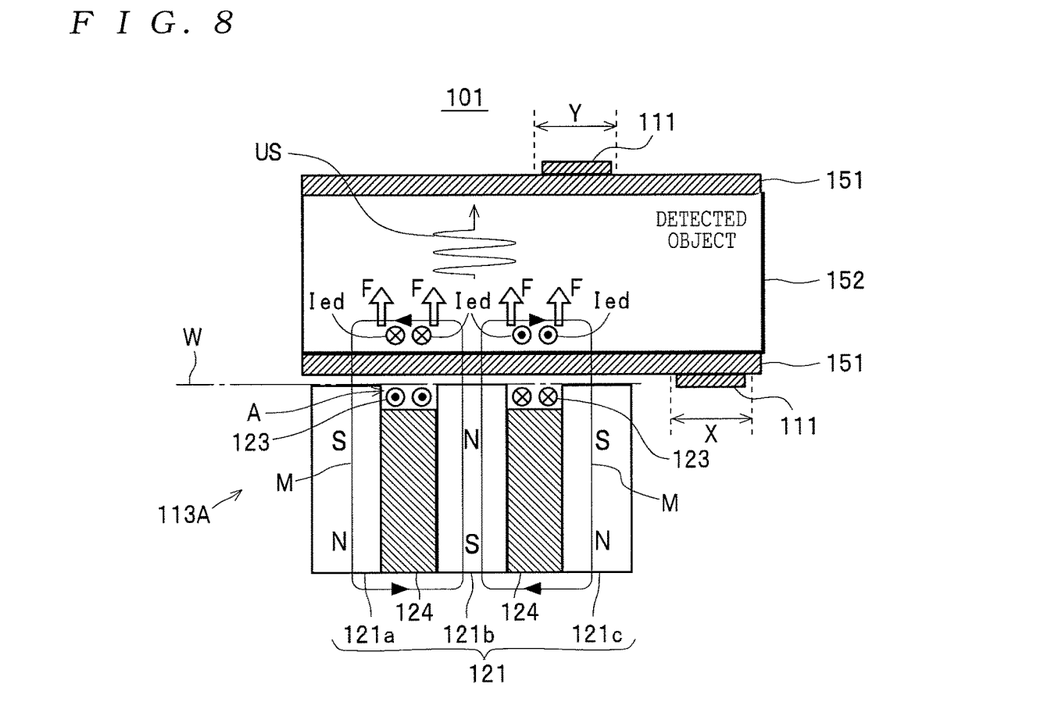
FIG. 8 is a diagram useful in explaining the configuration of another ultrasonic excitation unit.

Here, as depicted in FIGS. 5 and 7, the detected object 152 is an electric conductor, and a position that forms one part of the surface of the detected object 152 may be covered with the insulator 151 or, as depicted in FIG. 8, the entire surface may be covered with the insulator 151 (as one example, the detected object 152 may be the core of a covered electrical cable whose entire outer circumferential surface is covered with an insulating covering). The insulator 151 may have a single-layer construction composed of one type of insulating material, or may have a multi-layer construction where a plurality of layers composed of insulating materials of respectively different types are laminated.

By using the configuration described later, the detection electrode 111 is disposed so as to be capable of directly contacting the surface of the insulator 151 that covers the detected object 152.

As one example, the vibration circuit 112 generates and outputs a reference signal S11 of a certain frequency (predetermined frequency) in a range of around 10 kHz (a frequency higher than an audible range) to several MHz. To do so, the vibration circuit 112 is capable of using a configuration that continuously outputs the reference signal S11 during operation, of using a configuration that intermittently and outputs cyclically for a certain period at a time, and of using a configuration that outputs in bursts of a certain length only during measurement. As examples, the vibration circuit 112 outputs a signal that is any of a square wave signal, a triangular wave signal, and a sine wave signal as the reference signal S11. Note that in place of a configuration that generates and outputs the reference signal S11 of a certain frequency as described above, as examples the vibration circuit 112 may use a configuration that generates and outputs a sweep signal whose frequency changes with time in a range between a lower limit frequency and an upper limit frequency that are set in advance as the reference signal S11 or a configuration that generates and outputs a random signal (noise signal) whose frequency changes randomly with time as the reference signal S11.

Figure 6:
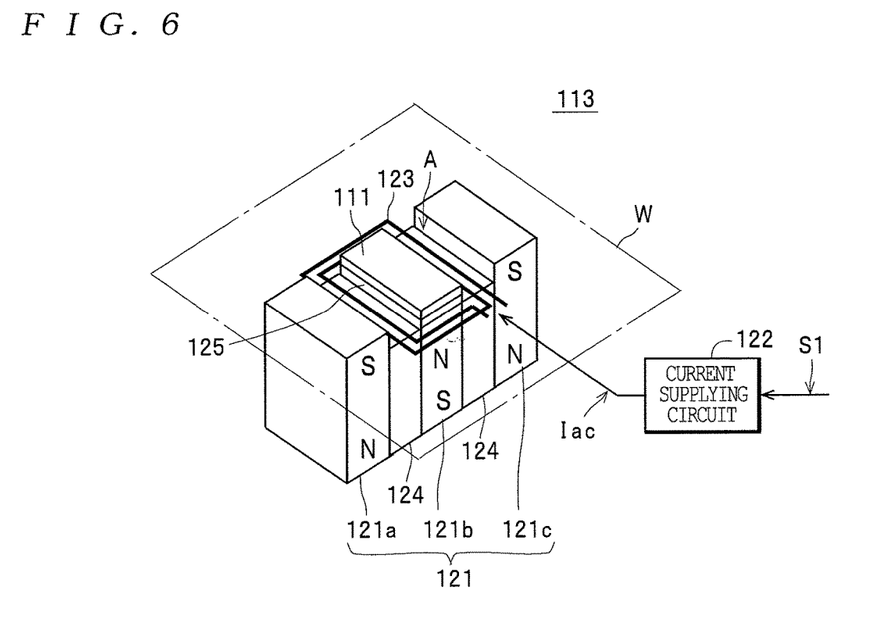
FIG. 6 is a perspective view of a detection electrode and an ultrasonic excitation unit.

As depicted in FIG. 5, by applying static magnetic fields M to the detected object 152 and having eddy currents Ied generated in the detected object 152 at application position of the static magnetic fields M, the ultrasonic excitation unit 113 induces ultrasound US that vibrates in a direction that intersects the surface at the application position (i.e., the depth direction) inside the detected object 152. In the present embodiment, as one example, as depicted in FIGS. 6 and 7, the ultrasonic excitation unit 113 includes a magnet 121 which generates the static magnetic fields M and applies the static magnetic field M to the detected object 152 to generate static magnetic fields M along the surface at the application position on the inside of the detected object 152 at the application position, a current supplying circuit 122 that generates, based on a reference signal S11, an AC current Iac with the same frequency as the reference signal S11, and a coil 123 that is supplied with the AC current Iac from the current supplying circuit 122 and generates the eddy currents Ied at the application position (the surface of the application position) described above of the detected object 152.

In the present embodiment, the magnet 121 includes three magnets (in the present embodiment, permanent magnets as one example) 121a, 121b, and 121c (a magnet 121a as a second magnet, a magnet 121b as a first magnet, and a magnet 121c as a third magnet). The magnets 121a, 121b, and 121c are respectively formed of column-like bodies (cylinders or polygon prisms such as rectangular prisms, in the present embodiment, rectangular prisms as one example) and have both end portions magnetized with different polarities at as magnetic poles. The magnets 121a, 121b, and 121c are disposed in a line with insulators 124 disposed in between. The polarities of end portions on the same side of the magnets 121a, 121b, and 121c (or "first end portions" for the present invention, the upper end portions in FIG. 5, the end portions on the application position side described above) are such that the polarity of the center magnet 121b (an N pole for example in the present embodiment) differs to the polarities of the other two magnets 121a and 121c (an S pole for example in the present embodiment).

Note that the magnets 121a, 121b, and 121c can also be constructed of electromagnets instead of permanent magnets. Also, although not illustrated, in place of a configuration where two separately formed magnets 121a and 121c are disposed on both sides of the center magnet 121b (a configuration where two magnets 121a and 121c are disposed so as to sandwich the center magnet 121b), it is possible to use a configuration where only one of the two magnets 121a and 121c is disposed on one side of the center magnet 121b or a configuration where the two magnets 121a and 121c are formed of a single hollow cylindrical magnet and the magnet 121b is disposed on the axis of such cylindrical magnet.

Also, in the present embodiment, as one example the magnets 121a and 121c on both sides are configured so that the end surfaces of first end portions are positioned on the same virtual plane W. Also, the center magnet 121b and the insulators 124 positioned on both sides of the magnet 121b are configured so that the end surfaces of the respective first end portions (the upper end portions in FIGS. 6 and 7) are depressed by substantially the same distance from the virtual plane W (the end surfaces of the first end portions of the magnets 121a and 121c on both sides). With this configuration, a hollow portion A with a substantially fixed depth is formed between the respective first end portions of the magnets 121a and 121c on both sides.

The coil 123 is constructed of a ring-shaped flat coil, for example, and is disposed in the vicinity of the first end portion of the magnet 121b. More specifically, the coil 123 is disposed at a position which is in the vicinity of the first end portion of the magnet 121 and is inside the hollow portion A so that the end surface of the first end portion of the magnet 121b is visible from a center portion of the coil 123 (i.e., a hole formed in the center of the coil 123), with the coil 123 parallel with the virtual plane W.

Also, as one example in the present embodiment, the detection electrode 111 is disposed on the end surface of the first end portion of the center magnet 121b with an insulator 125 placed in between. Also, by adjusting at least one of the depth of the hollow portion A, the thickness of the insulator 125, and the thickness of the detection electrode 111, the detection electrode 111 is configured in a state where the surface (the upper surface of the detection electrode 111 in FIGS. 6 and 7) is positioned on the virtual plane W or in a state where the surface protrudes slightly from the virtual plane W (as one example in the present embodiment, the former state).

By using this configuration, with the voltage detection apparatus 101, by bringing the ultrasonic excitation unit 113 close to and in contact with the insulator 151 from the first end portion side of the magnets 121a, 121b, and 123b, it is possible to place the detection electrode 111 in direct contact with the surface of the insulator 151. That is, the ultrasonic excitation unit 113 is configured so that the magnets 121a, 121b, and 121c are disposed perpendicular to the insulator 151 (that is, perpendicular to the application position of the detected object 152).

As one example, the current-to-voltage converter circuit 114 includes an operational amplifier 114a and a feedback resistor 114b as a feedback circuit. The non-inverting input terminal (first input terminal) of the operational amplifier 114a is connected to a reference potential (ground) so as to be set at a reference voltage (zero volts), the inverting input terminal (second input terminal) is connected to the detection electrode 111, and the feedback resistor 114b is connected between the inverting input terminal and the output terminal. Note that although a feedback circuit is constructed by a single feedback resistor 114b as one example in the present embodiment, it is also possible to construct a feedback circuit using a series or parallel circuit with a plurality of resistors or a series-parallel circuit that is a combination of a series circuit and a parallel circuit.

The current-to-voltage converter circuit 114 converts the detection current I to the detection voltage signal V2 and outputs the detection voltage signal V2. The detection current I flows from the detected object 152 via the detection electrode 111 to the reference potential due to a potential difference Vdi (since the reference voltage in the present embodiment is zero volts, the voltage V1) between the voltage V1 of the detected object 152 and the voltage of the detection electrode 111 (since the input terminals of the operational amplifier 114a are virtually shorted, the reference voltage) when the value of the capacitance of the insulator 151 positioned between the detected object 152 and the detection electrode 111 varies due to the vibration generated in the detected object 152 based on the ultrasound US generated in the detected object 152 by the ultrasonic excitation unit 113. The detection current I has a current value in keeping with the magnitude of the potential difference Vdi. That is, the current-to-voltage converter circuit 114 converts the detection current I whose amplitude is modulated in keeping with the potential difference between the voltage V1 of the detected object 152 and the voltage (reference voltage) of the detection electrode 111 (a current that is synchronized with the vibration generated in the detected object 152) to the detection voltage signal V2.

In this case, since the detection current I is generated by changing the value of the capacitance of the insulator 151 with the frequency of the vibration generated in the detected object 152 (that is, the frequency of the ultrasound US, which is the same frequency as the frequency of the AC current Iac and the reference signal S11, hereinafter also referred to as the "vibration frequency"), the detection current I is generated as an AC signal with the same frequency as the vibration frequency and an AC signal whose amplitude is modulated to a level in keeping with the potential difference Vdi (in the present embodiment, the voltage V1) described above. This means that the detection voltage signal V2 is outputted from the current-to-voltage converter circuit 114 as an AC signal with the same frequency as the vibration frequency and an AC signal whose amplitude is modulated to a level in keeping with the potential difference Vdi (in the present embodiment, the voltage V1).

Note that although the current-to-voltage converter circuit 114 that is constructed of the operational amplifier 114a and the feedback resistor 114b and is capable of detecting the detection current I, which typically has an extremely small (minute) amplitude, and converting the detection current I to the detection voltage signal V2 has been described above as an example, the present invention is not limited to such. As one example, when it is desirable to realize the current-to-voltage converter circuit 114 using a simpler configuration, in place of the configuration described above, although not illustrated it is also possible to use a configuration with a resistor with one end connected to the detection electrode 111 and the other end connected to the reference potential (ground). With a current-to-voltage converter circuit 114 of this configuration, the resistor converts the detection current I, which flows from the detected object 152 via the detection electrode 111 to the reference potential (reference voltage), to the detection voltage signal V2. At one end of the resistor, the converted detection voltage signal V2 is outputted to the buffer amplifier 115, described later.

The buffer amplifier 115 is constructed of an amplifier with a high input impedance and a low output impedance, and inputs the detection voltage signal V2 outputted from the current-to-voltage converter circuit 114 with a low impedance. The detector circuit 116 is constructed of a synchronized detection circuit, for example, and by detecting the detection voltage signal V2 inputted from the buffer amplifier 115 in synchronization with a synchronization signal S2 inputted from the phase adjusting circuit 117, detects (extracts) an amplitude component (DC component) of the detection voltage signal V2 and outputs as a detection output (voltage signal) V3. This detector circuit 116 is constructed of any of a multiplier, a selector switch (multiplexer) constructed of an analog switch, and a correlator. Note that it is also possible for the detector circuit 116 to be constructed of an envelope detection circuit, and since the synchronization signal S2 is not necessary when such configuration is used, it is possible to omit the phase adjusting circuit 117.

The phase adjusting circuit 117 inputs and delays the reference signal S11 from the vibration circuit 112 and outputs the reference signal S11 as the synchronization signal S2. The phase adjusting circuit 117 is configured so as to be capable of adjusting the delay between the synchronization signal S2 and the reference signal S11. The delay is adjusted in advance so that the phase of the detection voltage signal V2 as an AC signal inputted into the detector circuit 116 and the phase of the synchronization signal S2 match.

As examples, the output circuit 118 is constructed of a voltmeter that detects and displays the voltage value of the detection output V3, a buffer circuit that inputs the detection output V3 and outputs with a low impedance, or an A/D converter that carries out A/D conversion of the detection output V3 and outputs voltage data that indicates the voltage value of the detection output V3.

Next, a detection operation for the voltage V1 of the detected object 152 carried out by the voltage detection apparatus 101 will now be described. Note that the voltage V1 may be a DC voltage or may be an AC voltage. As one example, it is assumed in the present embodiment that the voltage V1 is a DC voltage.

First, as depicted in FIGS. 5 and 7, by placing the end surfaces of the first end portions of the magnets 121a and 121c that construct the ultrasonic excitation unit 113 in contact (tight contact) with the surface of the insulator 151 that covers the detected object 152, the detection electrode 111, which is positioned on the same virtual plane W as such end surfaces, is placed in contact (tight contact) with the surface of the insulator 151. When doing so, to improve the contact between the insulator 151 and the detection electrode 111, other insulators (for example, an insulating sheet or a gel-type insulator) may be interposed between the members.

By doing so, as depicted in FIG. 7, the static magnetic field M that is generated between the first end portions of a first pair of magnets 121a and 121b out of the magnets 121a, 121b, and 121c (i.e., between end portions that are magnetized to respectively different polarities) and the static magnetic field M that is generated between the first end portions of another pair of the magnets 121b and 121c (between end portions that are magnetized to respectively different polarities) are applied via the insulator 151 to the application position of the detected object 152. Here, since the first end portions of the first pair of magnets 121a and 121b are disposed apart from each other along the surface of the insulator 151 (which is also "along the surface of the detected object 152") and the first end portions of the other pair of magnets 121b and 121c are disposed apart from each other along the surface of the insulator 151 (which is also "along the surface of the detected object 152"), as depicted in FIG. 7, static magnetic fields M on the inside of the application position of the detected object 152 are generated in a direction along the surface of the application position.

Also, in the ultrasonic excitation unit 113, since the magnets 121a and 121c (i.e., magnets that are separate to the magnet 121b) for which the polarity at the first end portions differs to the polarity of the first end portion of the magnet 121b) are disposed so that the respective first end portions are adjacent to the magnet 121b, it is possible to generate strong static magnetic fields M inside the detected object 152.

In this state, when the reference signal S11 is outputted from the vibration circuit 112, in the ultrasonic excitation unit 113, the current supplying circuit 122 generates the AC current Iac based on the reference signal S11 and supplies the AC current Iac to the coil 123. The coil 123 receives the supply of the AC current Iac and generates an alternating magnetic field, not illustrated. The coil 123 is disposed inside the hollow portion A formed between the first end portions of the magnets 121a and 121c on both sides as described above so as to be parallel with the virtual plane W. This means that the alternating magnetic field generated by the coil 123 is applied to the surface of the application position of the static magnetic fields M on the detected object 152. Due to this alternating magnetic field, the eddy currents Ied are generated at the surface of the application position on the detected object 152.

In this way, since the eddy currents Ied are generated at the surface of the application position of the static magnetic fields M on the detected object 152 (the position where the static magnetic fields M are generated in a direction along the surface of the detected object 152), based on the static magnetic fields M and the eddy currents Ied, Lorentz forces F are generated along a direction that intersects the surface of the application position of the detected object 152 as depicted by the unshaded arrows (i.e., in the depth direction of the detected object 152, that is, a direction perpendicular to the surface of the application position). Since the direction of the Lorentz forces F is reversed in every half cycle of the AC current Iac, based on the Lorentz forces F, ultrasound US with the same frequency as the AC current Iac is induced inside the detected object 152 along a direction that intersects the surface of the application position (i.e., the depth direction of the detected object 152). Also, due to the generation of the ultrasound US, vibration with the same frequency as the AC current Iac is generated in the detected object 152 in a direction that intersects the surface of the application position (i.e., the depth direction of the detected object 152).

Since the vibration (mechanical vibration) is transmitted to the insulator 151 that is in contact with the detected object 152, the insulator 151 also vibrates with the same frequency (vibration frequency) as the detected object 152. Here, since the distance or density (the density of the insulator 151) between the detected object 152 and the detection electrode 111 will vary with the same frequency as the vibration frequency of the insulator 151 (which is also the vibration frequency of the detected object 152), the value of the capacitance of the insulator 151 positioned between the detected object 152 and the detection electrode 111 will also vary with the same frequency as the vibration frequency. Due to the variation in the value of the capacitance, the detection current I, which is an AC current whose amplitude is modulated to a level in keeping with the potential difference Vdi (the voltage V1) and whose frequency is the same as the vibration frequency, flows on a path including the detected object 152, the detection electrode 111, and the feedback resistor 114b of the current-to-voltage converter circuit 114.

The current-to-voltage converter circuit 114 converts the detection current I to the detection voltage signal V2 and outputs the detection voltage signal V2. The buffer amplifier 115 inputs the detection voltage signal V2 outputted from the current-to-voltage converter circuit 114 and outputs with a low impedance. On the other hand, by inputting and delaying the reference signal S11, the phase adjusting circuit 117 outputs the synchronization signal S2 to a detector circuit 116.

By detecting the detection voltage signal V2 outputted from the buffer amplifier 115 in synchronization with the synchronization signal S2 outputted from the phase adjusting circuit 117, the detector circuit 116 detects the amplitude component (DC component) of the detection voltage signal V2 in a state where external disturbances have little influence and outputs to the output circuit 118 as the detection output (voltage signal) V3. Here, the amplitude component (DC component) of the detection voltage signal V2 detected as the detection output V3 changes in accordance with the potential difference Vdi (in the present embodiment, the voltage V1) described above.

When constructed of an analogue voltmeter, for example, the output circuit 118 inputs the detection output (voltage signal) V3 and, based on the voltage value of the detection output V3 (a voltage value that is proportional to the potential difference Vdi (the voltage V1)), moves a pointer to a value indicating the voltage value of the potential difference Vdi (the voltage V1), thereby outputting in a state where the voltage value of the potential difference Vdi (the voltage V1) can be visually confirmed. When constructed of a buffer circuit, for example, the output circuit 118 inputs the detection output V3 and outputs to the periphery with a low impedance (i.e., outputs to an external measuring instrument or the like so that the voltage value of the potential difference Vdi (the voltage V1) can be detected based on the detection output V3). Also, when constructed of an A/D converter, for example, the output circuit 118 inputs the detection output V3 and outputs voltage data indicating the voltage value of the detection output V3 (which is also voltage data indicating the voltage value of the potential difference Vdi (the voltage V1)) to an internally-provided processing unit (not illustrated) or an external processing apparatus.

In this way, with the voltage detection apparatus 101, due to the ultrasonic excitation unit 113 causing the detected object 152 to vibrate by inducing the ultrasound US inside the detected object 152 and causing the insulator 151 that is in contact with the detection electrode 111 to vibrate with the generated vibration, the detection current I is generated and the voltage V1 of the detected object 152 is detected based on the detection current I. In this way, according to the voltage detection apparatus 101, it is possible to detect the voltage V1 of the detected object 152 contactlessly (i.e., without the detection electrode 111 being placed in direct contact with the detected object 152), even when the insulator 151 is present between the detected object 152 and the detection electrode 111.

Also, according to the voltage detection apparatus 101, the ultrasonic excitation unit 113 includes the magnet 121 that generates the static magnetic fields M along the surface at the application position of the static magnetic fields M and inside the detected object 152 at the application position and the coil 123 that generates the eddy currents Ied in the detected object 152 based on the supplied AC current Iac. The ultrasonic excitation unit 113 induces the ultrasound US that vibrates inside the detected object 152 in a direction perpendicular to the surface of the application position (i.e., in the depth direction of the detected object 152). Accordingly, according to the voltage detection apparatus 101, since it is possible to generate vibration, which is capable of causing variation in the value of the capacitance of the insulator 151 with the highest efficiency, in the detected object 152 and the insulator 151, it is possible to increase the level of the detection current I flowing from the detected object 152 via the detection electrode 111 to the reference potential. As a result, it is possible to sufficiently increase the detection sensitivity for the voltage V1 of the detected object 152.

Also, with the voltage detection apparatus 101, the magnet 121 includes the central magnet 121b that has the coil 123 disposed in the vicinity of the first end portion as a pole on the application position side and the two magnets 121a and 121c whose first end portions as poles on the application position side are magnetized with different polarities to the first end portion of the magnet 121b and that are disposed on both sides of the magnet 121b so as to sandwich the first end portion of the magnet 121b.

Accordingly, with the voltage detection apparatus 101, since it is possible to generate static magnetic fields M along the surface of the detected object 152 inside the detected object 152 on both sides of an opposing position that opposes the first end portion of the central magnet 121b at the application position of the static magnetic fields M, it is possible to cause the static magnetic fields M to have a greater effect relative to the eddy currents Ied generated in the periphery of such opposing position. As a result, it is possible to generate stronger ultrasound US and in turn to generate stronger vibration inside the detected object 152. By doing so, according to the voltage detection apparatus 101 it is possible to significantly raise the level of the detection current I that flows from the detected object 152 via the detection electrode 111 to the reference potential. As a result, it is possible to significantly raise the detection sensitivity for the voltage V1 of the detected object 152.

According to the voltage detection apparatus 101, by having the detector circuit 116 detect the detection voltage signal V2 in synchronization with the synchronization signal S2 and output the detection output V3, it is possible to detect and output the detection output V3 in a state where external disturbances have little influence.

In addition, according to the voltage detection apparatus 101, since the current-to-voltage converter circuit 114 includes the operational amplifier 114a and a feedback resistor 114b, it is possible to detect the detection current I with high sensitivity and convert the detection current I to the detection voltage signal V2.

Note that although the above example uses a configuration where a hollow portion A is formed between the first end portions of the magnets 121a and 121c on both sides and the detection electrode 111 is disposed in the ultrasonic excitation unit 113 inside the hollow portion A (in the example described above, the ultrasonic excitation unit 113 is disposed on the end surface of the first end portion of the central magnet 121b with the insulator 125 in between), like the ultrasonic excitation unit 113A depicted in FIG. 8, it is also possible to use a configuration where the detection electrode 111 is separated. As one example, as depicted in FIG. 8, with the ultrasonic excitation unit 113A, although a configuration is used where the end surface of the first end portion of the magnet 121b is positioned on the virtual plane W and the first end portion of the magnet 121b advances into the hole formed in the center of the coil 123 (a configuration where the coil 123 is formed on the outer circumference of the first end portion), in the same way as the ultrasonic excitation unit 113 described above, it is also possible to use a configuration where the first end portion of the magnet 121b is depressed from the virtual plane W. Note that configurations that are the same as the ultrasonic excitation unit 113 described above have been assigned the same reference numerals and duplicated description is omitted.

By using the configuration described above, as indicated by the symbols X and Y in FIG. 8, it is possible to dispose the detection electrode 111 at a position on the surface of the insulator 151 that differs to the application position of the static magnetic fields M (the position X is a position on the same side as the application position and the position Y is a position on the opposite side to the application position).

Figure 9:
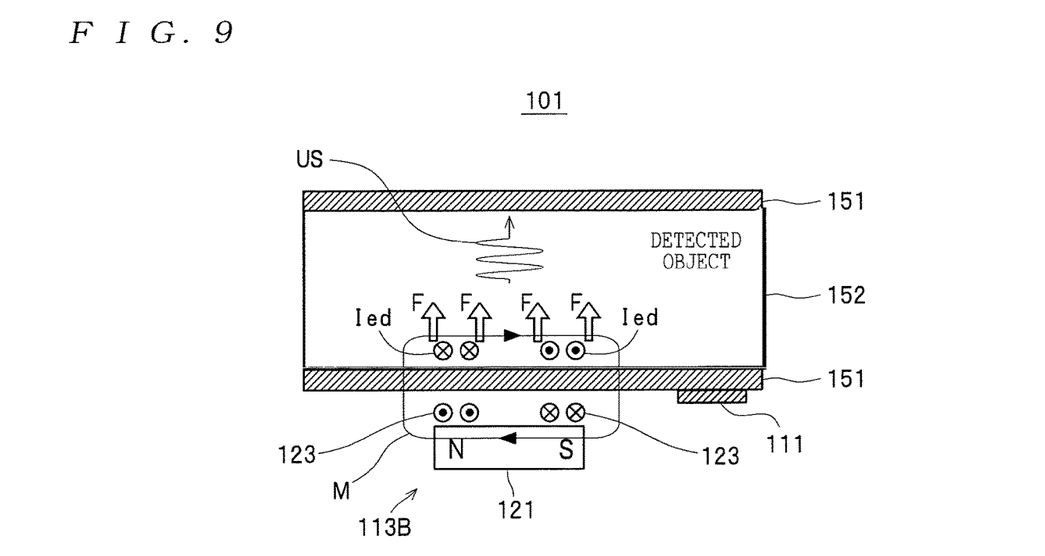
FIG. 9 is a diagram useful in explaining the configuration of another ultrasonic excitation unit.

Although the ultrasonic excitation units 113 and 113A described above use a configuration where the magnet 121 (the magnets 121a, 121b, and 121c) is disposed in a state where the magnet 121 is perpendicular to the surface of the application position of the detected object 152, like the ultrasonic excitation unit 113B depicted in FIG. 9, it is also possible to use a configuration where the magnet 121 is disposed in a horizontal state. With this configuration, although the strength of the static magnetic fields M generated inside the application position of the detected object 152 is weaker than with the ultrasonic excitation units 113 and 113A described above, it is still possible with this configuration to generate the static magnetic fields M inside the application position along the surface of the application position. Accordingly, since it is possible with the ultrasonic excitation unit 113B to generate ultrasound US along the depth direction of the detected object 152, it is possible to cause the detected object 152 to vibrate in the depth direction (a direction that intersects the surface of the application position, in this example, a perpendicular direction).

What is claimed is:

1. A voltage detecting apparatus that detects a detection voltage generated in a detected object covered by a first insulator, the voltage detecting apparatus comprising:
    a detection electrode that is disposed
        to contact the first insulator directly, or
        to contact a second insulator, aside from a gas, the second insulator disposed in contact with the first insulator;
    a vibrator that causes the first insulator to vibrate by contacting the first insulator or by contacting and vibrating the second insulator;
    a current-to-voltage converter circuit that converts a detection current to a detection voltage signal, the detection current flowing from the detected object via the detection electrode to a reference voltage in a state where the first insulator is being caused to vibrate, having an amplitude that is modulated in accordance with a potential difference between the detection voltage and the reference voltage, and being synchronized with vibration of the vibrator; and
    a detector circuit that detects a detection output indicating the potential difference from the detection voltage signal.

2. The voltage detecting apparatus according to claim 1, wherein the detector circuit detects the detection output by detecting the detection voltage signal in synchronization with a synchronization signal that is synchronized with the detection voltage signal.

3. The voltage detecting apparatus according to claim 1, wherein the current-to-voltage converter circuit includes an operational amplifier whose first input terminal is set at the reference voltage, whose second input terminal is connected to the detection electrode, which has a feedback circuit connected between the second input terminal and an output terminal, and which converts the detection current flowing in the feedback circuit to the detection voltage signal.

4. The voltage detecting apparatus according to claim 2, wherein the current-to-voltage converter circuit includes an operational amplifier whose first input terminal is set at the reference voltage, whose second input terminal is connected to the detection electrode, which has a feedback circuit connected between the second input terminal and an output terminal, and which converts the detection current flowing in the feedback circuit to the detection voltage signal.

5. The voltage detecting apparatus according to claim 1, further comprising a case which is formed of an insulating material and inside which the detection electrode, the vibrator, the current-to-voltage converter circuit, and the detector circuit are disposed, wherein the detection electrode is disposed on an inner surface of a first wall portion, out of a plurality of wall portions that construct the case, whose outer surface is placed in contact with the first insulator with the first wall portion as the second insulator, and the vibrator is fixed to an inner surface of a second wall portion out of the plurality of wall portions and causes the case to vibrate.

6. The voltage detecting apparatus according to claim 2, further comprising a case which is formed of an insulating material and inside which the detection electrode, the vibrator, the current-to-voltage converter circuit, and the detector circuit are disposed, wherein the detection electrode is disposed on an inner surface of a first wall portion, out of a plurality of wall portions that construct the case, whose outer surface is placed in contact with the first insulator with the first wall portion as the second insulator, and the vibrator is fixed to an inner surface of a second wall portion out of the plurality of wall portions and causes the case to vibrate.

7. The voltage detecting apparatus according to claim 3, further comprising a case which is formed of an insulating material and inside which the detection electrode, the vibrator, the current-to-voltage converter circuit, and the detector circuit are disposed, wherein the detection electrode is disposed on an inner surface of a first wall portion, out of a plurality of wall portions that construct the case, whose outer surface is placed in contact with the first insulator with the first wall portion as the second insulator, and the vibrator is fixed to an inner surface of a second wall portion out of the plurality of wall portions and causes the case to vibrate.

8. The voltage detecting apparatus according to claim 4, further comprising a case which is formed of an insulating material and inside which the detection electrode, the vibrator, the current-to-voltage converter circuit, and the detector circuit are disposed, wherein the detection electrode is disposed on an inner surface of a first wall portion, out of a plurality of wall portions that construct the case, whose outer surface is placed in contact with the first insulator with the first wall portion as the second insulator, and the vibrator is fixed to an inner surface of a second wall portion out of the plurality of wall portions and causes the case to vibrate.

9. The voltage detecting apparatus according to claim 1, further comprising a shield member that covers the detection electrode, the vibrator, the current-to-voltage converter circuit, and the detector circuit.

10. A voltage detecting apparatus that detects a detection voltage generated in a detected object which is covered by a first insulator, the voltage detecting apparatus comprising:

a detection electrode that is disposed
  to contact the first insulator directly, or
  to contact a second insulator, aside from a gas, the second insulator disposed in contact with the first insulator;

an ultrasonic excitation unit that applies a static magnetic field to the detected object and generates an eddy current at an application position of the static magnetic field on the detection object to induce ultrasound in the detected object in a direction that intersects a surface of the application position;

a current-to-voltage converter circuit that converts a detection current to a detection voltage signal, the detection current flowing from the detected object via the detection electrode to a reference voltage in a state where the ultrasound is being induced in the detected object, having an amplitude that is modulated in accordance with a potential difference between the detection voltage and the reference voltage, and being synchronized with the ultrasound; and a detector circuit that detects a detection output indicating the potential difference from the detection voltage signal.

11. The voltage detecting apparatus according to claim 10, wherein the ultrasonic excitation unit includes a magnet which generates the static magnetic field and applies the static magnetic field to the detected object to generate a static magnetic field along the surface on an inside of the detected object at the application position, and a coil that generates the eddy current in the detected object based on a supplied alternating current, and induces the ultrasound that vibrates in a direction perpendicular to the surface of the application position.

12. The voltage detecting apparatus according to claim 11, wherein the magnet includes: a first magnet that has the coil disposed in a vicinity of a magnetic pole on an application position side; and a second magnet and a third magnet that are disposed to sandwich the first magnet and have magnetic poles on an application position side polarized to a different polarity to the magnetic pole of the first magnet.

13. The voltage detecting apparatus according to claim 10, wherein the detector circuit detects the detection output by detecting the detection voltage signal in synchronization with a synchronization signal that is synchronized with the detection voltage signal.

14. The voltage detecting apparatus according to claim 11, wherein the detector circuit detects the detection output by detecting the detection voltage signal in synchronization with a synchronization signal that is synchronized with the detection voltage signal.

15. The voltage detecting apparatus according to claim 12, wherein the detector circuit detects the detection output by detecting the detection voltage signal in synchronization with a synchronization signal that is synchronized with the detection voltage signal.

16. The voltage detecting apparatus according to claim 10, wherein the current-to-voltage converter circuit includes an operational amplifier whose first input terminal is set at the reference voltage, whose second input terminal is connected to the detection electrode, which has a feedback circuit connected between the second input terminal and an output terminal, and which converts the detection current flowing in the feedback circuit to the detection voltage signal.

* * * * *